(12) United States Patent  (10) Patent No.: US 8,415,141 B2
You et al.  (45) Date of Patent: Apr. 9, 2013

(54) ENCLOSED UNIT FOR RAPID DETECTION OF A TARGET NUCLEIC ACID AMPLIFICATION PRODUCT

(76) Inventors: Qimin You, Hangzhou (CN); Lin Hu, Hangzhou (CN); Jiayong Gu, Hangzhou (CN); Qinhao Yu, Hangzhou (CN)

( * ) Notice: Subject to any disclaimer, the term of this patent is extended or adjusted under 35 U.S.C. 154(b) by 0 days.

(21) Appl. No.: 12/228,432

(22) Filed: Aug. 12, 2008

(65) Prior Publication Data

US 2009/0181388 A1  Jul. 16, 2009

Related U.S. Application Data

(60) Provisional application No. 60/964,993, filed on Aug. 17, 2007.

(51) Int. Cl.
*C12Q 1/68* (2006.01)
*C12M 1/34* (2006.01)

(52) U.S. Cl.
USPC .......... 435/287.2; 435/4; 435/6.1; 435/287.1; 422/512

(58) Field of Classification Search ............... 435/287.2, 435/4, 6.1, 287.6, 6, 6.11; 422/413, 410, 422/512, 554
See application file for complete search history.

(56) References Cited

U.S. PATENT DOCUMENTS 4,791,060 A * 12/1988 Chandler ................... 435/287.2
5,393,496 A * 2/1995 Seymour ..................... 422/413
5,415,839 A * 5/1995 Zaun et al. ..................... 422/64
5,955,351 A * 9/1999 Gerdes et al. .............. 435/287.2
5,976,888 A * 11/1999 Lee et al. ...................... 436/110
7,507,374 B2 * 3/2009 Gould et al. .................. 422/417
8,003,048 B2 * 8/2011 Clay et al. ....................... 422/63
8,273,312 B2 * 9/2012 Porat et al. ................... 422/550

* cited by examiner

*Primary Examiner* — William H Beisner
*Assistant Examiner* — Danielle Henkel
(74) *Attorney, Agent, or Firm* — G Kenneth Smith (57) ABSTRACT

The invention relates to a method for rapid detection of a target nucleic acid amplification product while preventing cross-contamination between target nucleic acid amplification products and avoiding false positives, comprising the steps of: a) leaving the reaction tube unopened after the amplification reaction is finished, so as to prevent the target nucleic acid amplification product from leaking out and resulting in contamination; b) placing the unopened reaction tube inside an enclosed unit, making the target nucleic acid amplification product be transferred to a test strip from the reaction tube in a physically enclosed environment; c) performing detection in a visual read-out manner, and determining the result; d) discarding the enclosed unit in a safety place as a whole without opening it after the detection. The invention also relates to a totally enclosed unit for detecting a target nucleic acid amplification product, and still relates to applications of the totally enclosed rapid detection unit in detection of infectious pathogens, food industry, agriculture, livestock husbandry, customs quarantine control, and determination of DNA.

11 Claims, 8 Drawing Sheets

SEQUENCE LISTING

```
<160> NUMBER OF SEQ ID NOS: 9

<210> SEQ ID NO 1
<211> LENGTH: 19
<212> TYPE: DNA
<213> ORGANISM: Neisseria gonorrhoeae

<400> SEQUENCE: 1
catactgtac catagcgtt                                                  19

<210> SEQ ID NO 2
<211> LENGTH: 19
<212> TYPE: DNA
<213> ORGANISM: Neisseria gonorrhoeae

<400> SEQUENCE: 2
attctgacat cccaagctt                                                  19

<210> SEQ ID NO 3
<211> LENGTH: 34
<212> TYPE: DNA
<213> ORGANISM: Neisseria gonorrhoeae

<400> SEQUENCE: 3
tccagacttg agtcggatgc ttcttaggga cgca                                 34
```

```
<210> SEQ ID NO 4
<211> LENGTH: 35
<212> TYPE: DNA
<213> ORGANISM: Neisseria gonorrhoeae

<400> SEQUENCE: 4
aatgcatgtg agtcggatgg atatgtccaa tccta                              35

<210> SEQ ID NO 5
<211> LENGTH: 19
<212> TYPE: DNA
<213> ORGANISM: Homo sapiens

<400> SEQUENCE: 5
tcactctcac tgcccaaaa                                                19

<210> SEQ ID NO 6
<211> LENGTH: 20
<212> TYPE: DNA
<213> ORGANISM: Homo sapiens

<400> SEQUENCE: 6
ggagaatggg ggataggtgt                                               20

<210> SEQ ID NO 7
<211> LENGTH: 20
<212> TYPE: DNA
<213> ORGANISM: Homo sapiens

<400> SEQUENCE: 7
cttcaccggc gcagtcattc                                               20

<210> SEQ ID NO 8
<211> LENGTH: 20
<212> TYPE: DNA
<213> ORGANISM: Homo sapiens

<400> SEQUENCE: 8
aggcgaggtt agcgaggctt                                               20

<210> SEQ ID NO 9
<211> LENGTH: 25
<212> TYPE: DNA
<213> ORGANISM: Homo sapiens

<400> SEQUENCE: 9
tcaaactacg aacgcactca cagtc                                         25
```

ENCLOSED UNIT FOR RAPID DETECTION OF A TARGET NUCLEIC ACID AMPLIFICATION PRODUCT

This application claims benefit under 35 USC §119(e) of the U.S. Provisional patent Application Ser. No. 60/964,993 filed Aug. 17, 2007.

TECHNICAL FIELD

The invention relates to an enclosed unit for detecting a target nucleic acid amplification product, and more specifically, to a method for rapid detection of a target nucleic acid sequence amplification product in an enclosed detection unit by utilizing nucleic acid thin-layer chromatography (test strip technique). The invention also relates to a rapid detection kit and the use of the kit for rapid detection of a target nucleic acid amplification product in a enclosed rapid detection unit. The methods, detection units and kits of the present invention can be utilized for the detection of infectious pathogens as well as other targets.

DESCRIPTION OF THE PRIOR ART

The Polymerase Chain Reaction (PCR) is a highly efficient technique for in vitro amplification of specific DNA fragments by using the principle of denaturation and renaturation of DNA in the presence of in vitro DNA polymerases.

With the rapid development in recent years, the PCR technique has been widely applied to various fields such as medicine, molecular biology, genetic engineering, oncology, forensic analysis, and so on. Under specific in vitro conditions, PCR is capable of amplifying a single copy of DNA fragment to tens of billions of copies within several hours, thereby achieving greatly improved sensitivity of specific gene detection. PCR has been widely applied to clinical medicine and life sciences for specific gene amplification and detection due to its strong specificity, high sensitivity, quick and simple operability, and good repeatability. For example, PCR detection of various pathogens has become one of the most important means for diagnosis of infectious diseases. However, due to the powerful efficiency of PCR amplification (usually about $10^{11}$ copies/μL are produced) and the method used for PCR product detection (agarose gel electrophoresis which requires that the amplification tube be opened), contamination between laboratory amplification products is extremely likely to occur, which may lead to false positives in subsequent detection. These false positives lead to confusing test results. Particularly in the detection of venereal diseases, there are even a series of problems regarding ethics, family disputes, and social and legal issues. The problems associated with clinical applications of PCR have been investigated and discussed by health authorities in various countries, and a series of provisions and regulations have been made on clinical applications of PCR. Meanwhile, the elimination of PCR false positives has been a major problem yet to be solved by researchers.

In order to prevent false positives resulting from contamination between laboratories of amplification products, PCR clinical diagnosis should be carried out in separate rooms for sample treatment, amplification, and detection. Open-tube detection should be avoided after amplification. At present, the most commonly used method for preventing contamination between laboratory amplification products is to adopt a uracil DNA N-glycosylase and deoxy uridine triphosphate (UNG-dUTP) system, which hydrolyzes uridine in a DNA fragment by utilizing the feature of UNG (glycosylase) as capable of hydrolyzing uridines in dUTP-contained DNA fragments. The hydrolyzed DNA breaks at the point it is hydrolyzed and can therefore not function as a template, thereby preventing contamination. To prevent contamination, however, the whole PCR system must utilizing dUTP instead of dTTP from the beginning. Furthermore, the cost of the anti-contamination reagent required by UNG-dUTP systems also limits the use of the reagent.

Fluorescence Quantitivative PCR is a technique which has been developed in recent years and takes advantage of the high efficiency of nucleic acid amplification by the PCR technique, the high specificity of the probe technique, and the high sensitivity and metering accuracy of the spectral technique, Fluorescence Quantitivative PCR overcomes the disadvantages of conventional PCR techniques such as cross-contamination, poor quantitation, low sensitivity of probe hybridization, and difficulty in controlling separation and elution conditions. This technique has, therefore has been widely applied to gene-based clinical diagnosis of diseases. Moreover, this technique is characterized by totally enclosed reaction, real-time detection of PCR amplification process, and avoids post amplification treatment on PCR products. These characteristics permits Fluorescence Quantitivative PCR to overcome the contamination issues that accompany conventional PCR techniques, and has resulted, in the adoption of this technique for nucleic acid detection especially for the clinical detection of pathogens. However, Fluorescence Quantitivative PCR requires highly skilled technicians to perform the technique. It also requires expensive instruments and reagents, and therefore this technique is not necessarily suitable for resource-limited hospitals.

Conventional PCR diagnosis is greatly restricted due to contamination between PCR amplification products. In order to avoid false positives resulting from laboratory contamination, the present invention describes a method, device and kit for rapidly detecting a target nucleic acid amplification product in a totally enclosed manner. The device of the present invention can be used in combination with the test strip technique for rapid detection of nucleic acids (see eg. Chinese Pat. App. No. 200610003429.1). The method of the present invention has advantages over the prior art methods in that it is simple, rapid and prevents contamination. The methods, device and kits of the present invention, have wide applicability in the field of life sciences for nucleic acid amplification detection for use in molecular biology laboratories, clinical diagnosis, detection of plant and animal diseases, customs quarantine control, medicolegal expertise, and the like.

In brief, the enclosed rapid detection unit for a target nucleic acid amplification product of the invention provides among other things a method for rapid detection of a target nucleic acid amplification product as well as a method for preventing cross-contamination between nucleic amplification products and avoiding false positives. Consequently, one goal of the present invention is to perform amplification product detection with little or no contamination.

Compared with conventional PCR detection techniques, the devices and methods of the present invention disclosed provide for enclosed detection. The detection unit is enclosed by both interior and exterior walls, that achieve a double sealing effect is achieved. The sealing of the device's inner core prevents the need to uncover the reaction tube which prevents the amplification product from leaking, thereby minimizing the chance of contamination from the amplification product and the occurrence of false positives in subsequent detection is prevented. The sealing of device's outer enclosure provides a substantially enclosed environment, and cannot be reopened once it is fastened during experiment, thereby preventing the amplification product inside the device from leaking out into the environment. The methods and devices of the present invention also provide high specificity, high sensitivity of target nucleic acid amplification product detection after amplification, simple and quick operability, and no instrumentation is required for detection after amplification since a simple test strip performs the detection.

SUMMARY OF THE INVENTION

The present invention provides a method for rapid detection of a target nucleic acid amplification product while preventing cross-contamination between target nucleic acid amplification products thereby avoiding false positives.

The present invention also provides an enclosed device for rapid detection of a product of PCR amplification, isothermal amplification, or other amplification processes by using a test strip for nucleic acid detection.

The present invention provides devices and methods for detection of a target nucleic acid amplification product comprising a cassette having a port into which a container containing the target nucleic acid amplification product in a fluid is placed such that a portion of the container is exposed, a sealable outer casing into which the cassette is placed and which completely encompasses the cassette when the outer casing is sealed, a cutting device that punctures the exposed portion of the container when the sealable outer casing is sealed to release the fluid and a detection strip in proximity to the container such that the liquid contacts the detection strip when the tube is punctured.

The devices of the present invention include enclosed devices for detection of a target nucleic acid amplification product, comprising an inner core and an outer casing wherein the inner core comprises a fixing case and a base, the fixing case having two ports respectively for housing washing buffer vacuoles and a reaction tube containing an amplification product, the base comprising a washing buffer container having a vacuole puncture needle, an amplification product container having a blade, a sealing diaphragm, a piece of glassfiber paper, and a test strip sealing part having a test strip sealed therein and a transparent window and wherein the outer casing comprises a handle cover, a fixing case pressing part, a washing buffer vacuole extruding part, and a transparent window.

The invention detects an amplification product by using the totally enclosed detection unit in combination with the test strip technique for rapid detection of nucleic acids. This method is simple and rapid in operation and free of contamination, and is an innovation of amplification product detection. The invention can be used in combination with isothermal amplification techniques to develop a novel platform for rapid detection of nucleic acids, whereby qualitative and semi-quantitative detection of nucleic acids can be realized with no contamination to laboratories. As a result of its unique characteristics, the invention can be made more widely applicable to clinical disease diagnosis and screening, as well as other fields of life sciences.

The devices of the present invention ensure an enclosed state for detection and analysis of a nucleic acid amplification product, thus the risk of cross-contamination with methods for nucleic acid detection after conventional amplification is significantly decreased. Meanwhile, the method offers advantages in simple and quick operability, decreased cost of detection, as well as accelerated acquisition and improved reliability of detection results. By applying the totally enclosed device for rapid detection of a target nucleic acid amplification product, the accuracy of the results can be greatly enhanced, and the overall cost of medical care can be reduced. Owning to simple and rapid operability, low cost, and the ability to prevent amplicon cross-contamination in laboratories, the methods and devices of the present invention will greatly benefit technologists working in the field of life sciences in the detection of target nucleic acid amplification products.

DETAILED DESCRIPTION OF THE INVENTION

The present invention provides methods, devices and kits for detection of a product of PCR amplification, isothermal amplification, or other amplification processes in an enclosed unit. In addition to simple and quick operability, the method is advantageous in its ability to prevent false positives resulting from laboratory contamination between amplification products. The ability to decrease or eliminate false positives greatly increases the reliability of in vitro diagnostic reagents.

According to a preferred embodiment of the present invention, the enclosed device utilized in methods of the present invention cannot be reopened once it has been closed so as to prevent the product inside from leaking out accidentally and contaminating other PCR reactions.

According to a more preferred embodiment of the invention, the step b) in the above method comprises opening the reaction tube as well as a washing buffer tube in a physically enclosed environment, so that the target nucleic acid amplification product is transferred to the test strip under the lead of the washing buffer.

The devices of the present invention provide for detection of a target nucleic acid amplification product comprising a cassette having a port into which a container containing the target nucleic acid amplification product in a fluid is placed such that a portion of the container is exposed, a sealable outer casing into which the cassette is placed and which completely encompasses the cassette when the outer casing is sealed, a cutting device that punctures the exposed portion of the container when the sealable outer casing is sealed to release the fluid and a detection strip in proximity to the container such that the liquid contacts the detection strip when the tube is punctured.

Figure 1:
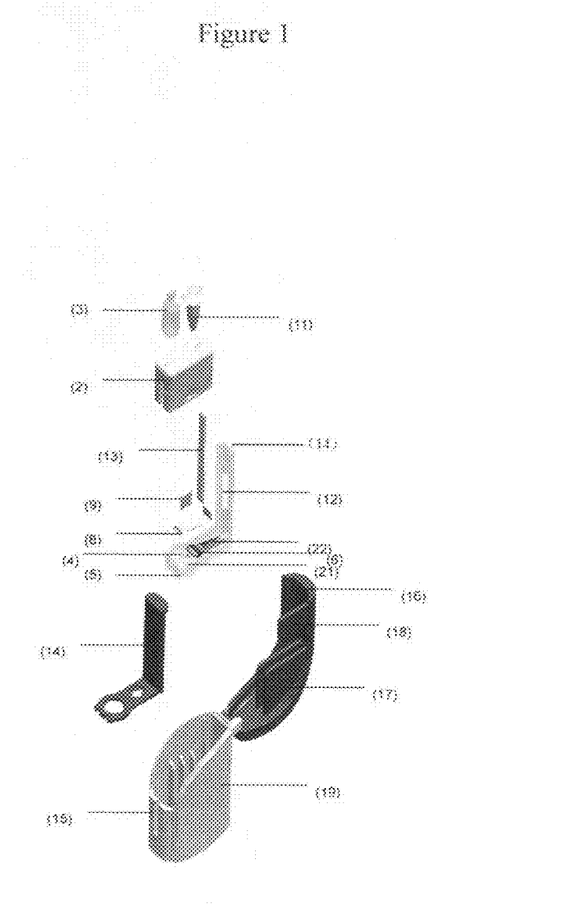
FIG. 1 is a schematic diagram of the contents of a preferred embodiment of the totally enclosed device for rapid detection of a target nucleic acid amplification product.

A preferred embodiment of the present invention is presented in FIG. 1. The device for rapid detection of a target nucleic acid amplification product, comprises an inner core (1) and an outer casing (15), wherein the inner core (1) comprises a fixing case (2) and a base (5), the fixing case (2) having two openings respectively for housing washing buffer vacuoles (3) and a reaction tube (11) containing an amplification product (7), the base (5) comprises a washing buffer container (21) having a vacuole puncture needle (4), an amplification product container element (22) having a cutting or piercing element such as a blade (9), a sealing diaphragm (6), a piece of glassfiber paper (8); and a test strip sealing part (14) having a test strip (13) sealed therein and a transparent window (12); and the outer casing (15) comprises a handle cover (16), a fixing case pressing part (17), a washing buffer vacuole extruding part (18), and a transparent window (20).

The invention provides devices that are enclosed for rapid detection of a target nucleic acid amplification product, comprising an inner core (1) and an outer casing (15), wherein the inner core (1) comprises a fixing case (2) and a base (5), the fixing case (2) being provided with two openings respectively for housing washing buffer vacuoles (3) and a reaction tube (11) containing an amplification product (7), the base (5) comprises a washing buffer container (21) having a vacuole puncture needle (4) for puncturing the washing buffer vacuoles (3), an amplification product container element (22) having a blade (9) for cutting the reaction tube (11), a sealing diaphragm between the units (21) and (22), a piece of glassfiber paper (8) disposed in the container elements (21) and (22) and connected to the bottom of a test strip (13), and a test strip sealing part having the test strip (13) sealed therein and a transparent window (12); and the outer casing (15) comprises a handle cover (16), a fixing case pressing part (17), a washing buffer vacuole extruding part (18), and a transparent window (20) in parallel with the transparent window (12).

In one preferred embodiment of the invention, the enclosed detection unit further comprises a sealing ring positioned between the hole for housing the reaction tube (11) and the base (5), which ensures an intimate and sealed contact thereat, and that the amplification product will not flow back into the fixing case (2).

In another preferred embodiment of the invention, the enclosed detection unit further comprises a sealing diaphragm (6) structured as three layers alternating vertically to ensure that the amplification product will not flow back, while being mixed with the washing buffer which flows in a single direction and is absorbed by the test strip (13).

In still another preferred embodiment of the invention, the totally enclosed detection device further comprises an outer casing which constitutes a totally enclosed environment, and cannot be reopened once it is fastened down during the experiment, so as to prevent the amplification products inside the device from leaking out accidentally.

In a more preferred embodiment of the invention, the totally enclosed detection unit further comprises a sealing ring (10) positioned between the opening for housing the reaction tube (11) and the base (5), which ensures an intimate and sealed contact, and that the amplification product will not flow back into the fixing case part (2). The sealing diaphragm (6) is structured as three layers alternating vertically to ensure that the amplification product will not flow back, while being mixed with the washing buffer flowing in a single direction and absorbed by the test strip (13). The outer casing (15) constitutes an enclosed environment, and in preferred embodiments the outer casing cannot be reopened once it is fastened down during the experiment, so as to prevent the amplification products inside the device from leaking out accidentally.

Figure 2:
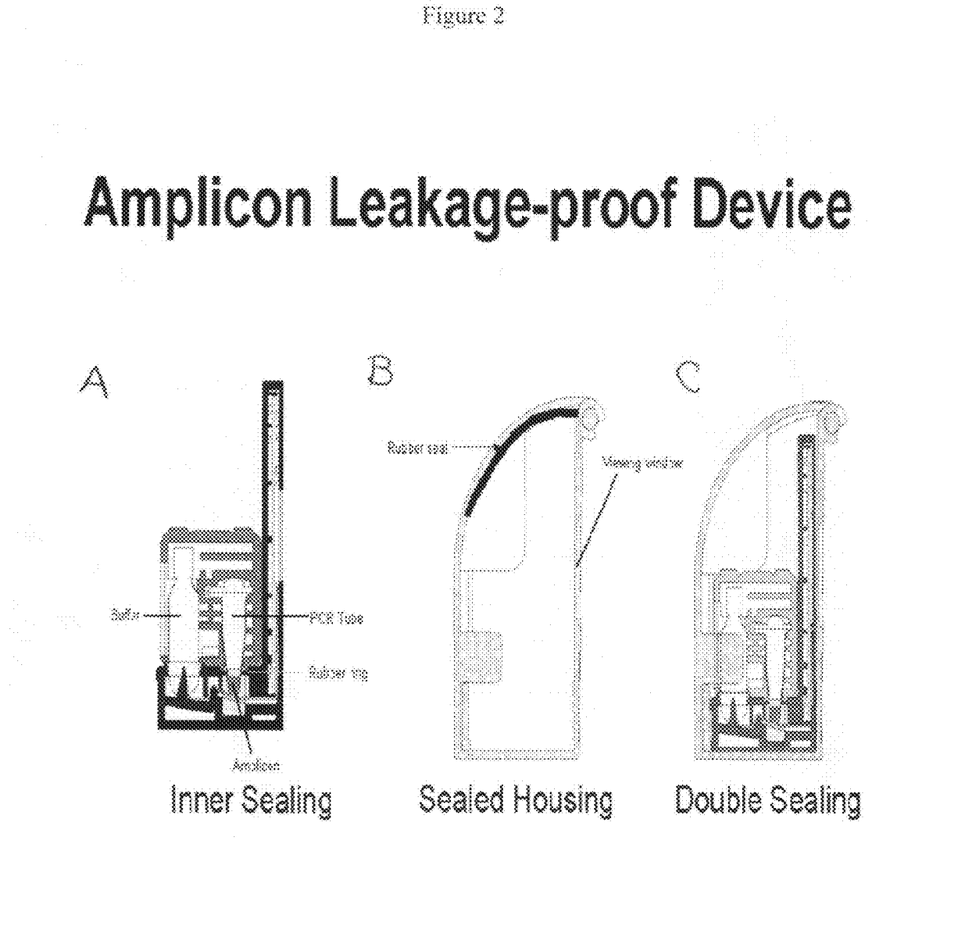
FIGS. 2A-C are illustrations of embodiment of the totally enclosed device for rapid detection of a target nucleic acid amplification product.

FIG. 2 illustrates the structure of a preferred totally enclosed device for rapid detection of a target nucleic acid amplification product according to the invention.

The methods of the present invention are carried out in an enclosed state, therefore, contamination to laboratories from amplification products is prevented because detection is carried out in a physically isolated manner, thereby increasing accuracy of the test. The term "enclosed" means that the devices of the invention are sealed. The purpose in sealing the device is to prevent amplification products from leaking out of the device and contaminating the surrounding environment. The devices of the present invention may have single layers or multiple layers of sealing such as an inner core and outer casing as shown in FIGS. 2 and 3.

Devices of the present invention can be used for detecting amplification products in a variety of ways one of which is described below:

An unopened reaction tube (any contained that holds a amplification product will serve the role of a reaction tube, in a preferred embodiment the reaction tube is a PCR tube) can be placed inside the opening for housing the reaction tube in the fixing case (2) (wherein the washing buffer vacuoles (3) have already been provided in the opening for housing the washing buffer vacuole tube in advance). The fixing case part (2) is then placed inside the outer casing (15), wherein the sealing ring (10) positioned between the opening for housing the reaction tube and the base (5) ensures an intimate and sealed contact thereat The handle cover (16) of the detection unit is closed and the cover (16) of the detection unit is pressed until it is fastened, whereby the cutting instrument (eg. a blade (9)) on the base is subjected to a pressing force by the fixing case pressing part (17) so as to puncture or cut the reaction tube (11) containing the amplification product (7), and the washing buffer vacuole puncturing device (eg. puncture needle (4)) on the base is subjected to a force by the washing buffer vacuole extruding part (18) so as to puncture the plastic washing buffer vacuoles. Then, through capillary action the glassfiber paper (or any material that can have liquid transferred through it by capillary action) (8), the amplification product (7) and the washing buffer are absorbed into a sample pad in the test strip (13). The liquids move along the sample pad while being mixed together and move towards the end of the nucleic acid test strip T the liquid mixture moves from one end of the test strip to the other end of the test strip through capillary action the detection process is accomplished by a specific antigen-antibody reaction between the reaction liquid and the test line on the nucleic acid detection test strip The strip is left for a period of time, typically 10 minutes before the results from the detection strip are read. After observing the results the whole device may be discarded in a safety place.

Figure 3:
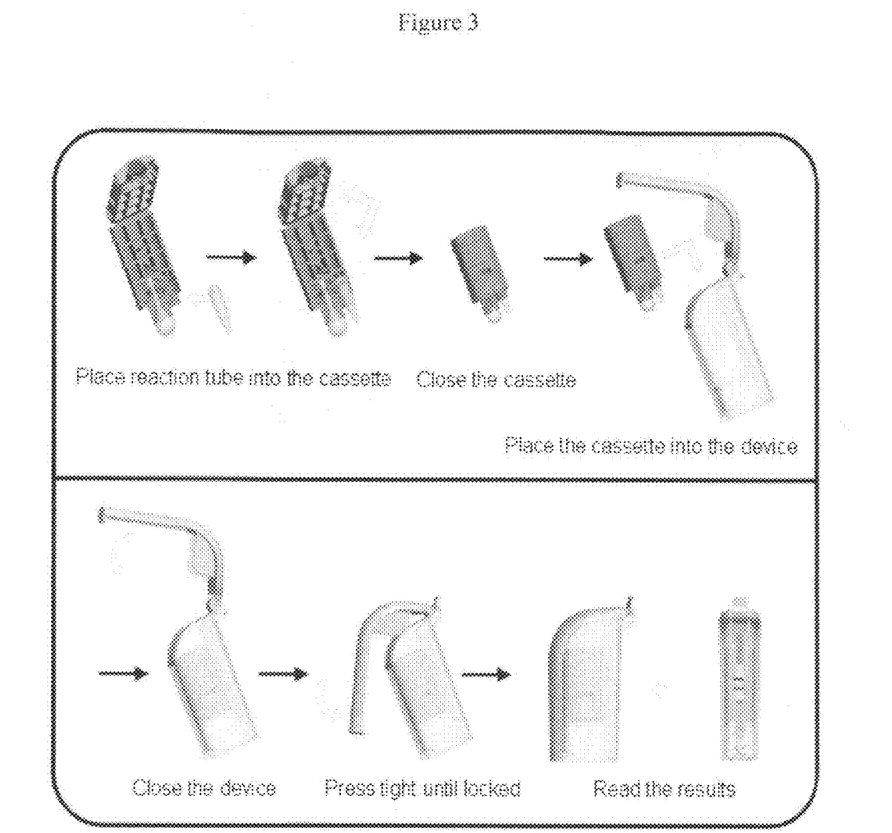
FIG. 3 is an illustration of the operation steps of the device.

FIG. 3 illustrates the operation steps of one embodiment of the detection device of the present invention. 1. Put the reaction tube with the amplification product into the fixing case, 2. close the fixing case to fix the tube, 3. place the fixing case into the outer casing, and 4. close the handle cover. The operation of these steps takes about 30 seconds and depending on the concentration of the sample and test strip used results can be seen in about 2 minutes. Reading the result after about 10-15 minutes provides good results as the background will clear and it is easier to see very weak signals.

The present invention also provides for methods for rapid detection of a target nucleic acid amplification product, which comprises detecting a nucleic acid sequence amplification product by using the above-mentioned totally enclosed unit for rapid detection of a target nucleic acid amplification product.

The present invention also provides methods for preventing cross-contamination between nucleic acid amplification products and provides methods for avoiding false positives, which comprises detecting a nucleic acid sequence amplification product by using the above-mentioned totally enclosed unit for rapid detection of a target nucleic acid amplification product.

One preferred method of the present invention includes a method of detecting a target nucleic acid amplification product which is retained in a detection device thereby avoiding contamination of a proximate space comprising the steps of:
a) placing the sealed container containing a target nucleic acid amplification product into the detection device;
b) closing the detection device such that the sealed container is punctured and the fluid containing the target nucleic amplification product is transferred to a sterile visual detection strip within the device such that the fluid is retained within the detection device; and
c) detecting the target nucleic acid amplification product.

Chinese App. No. 200610003429.1 describes the principle and method for the test strip detection of nucleic acids. Accordingly, basic methods of test strip technique for detecting proteins on the basis of immunoreaction can all be applied to the test strip detection of nucleic acids. The basic method for transforming a target nucleic acid amplification product to be detected into molecules or a molecular compound is characterized by labeling probes with antigens or haptens (hereinafter abbreviated as antigens), hybridizing the labeled specific probes with the target nucleic acid amplification product to be detected, so as to form a molecular compound with immunogenicity, which can be detected by methods similar to the test strip detection of proteins.

Figure 4:
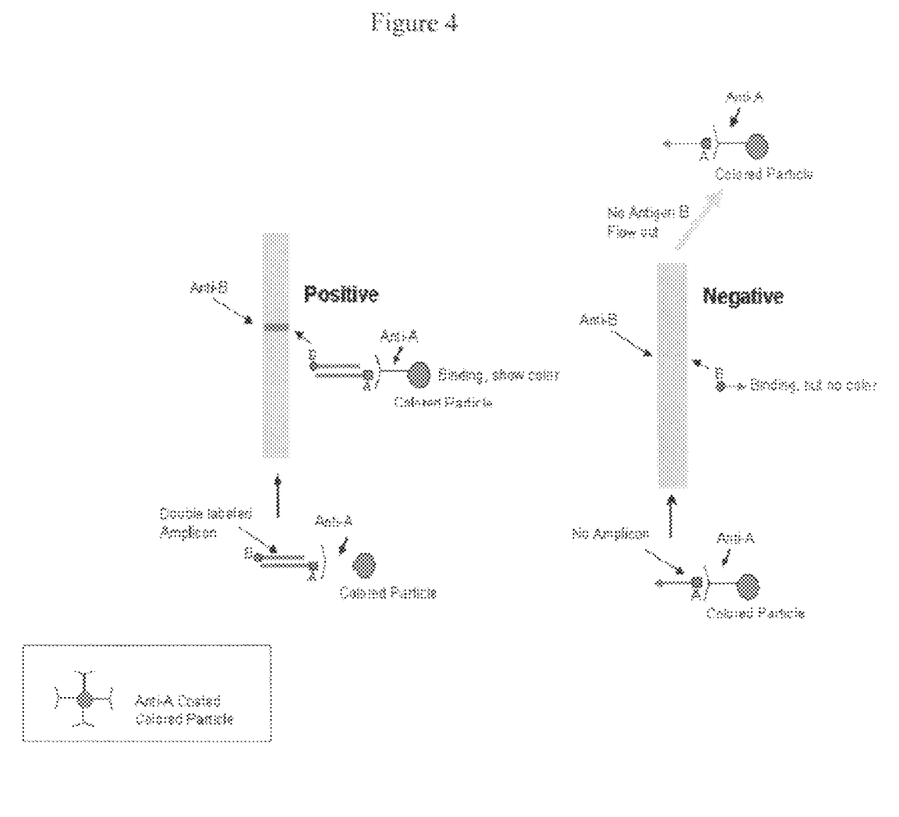
FIG. 4 is an illustration of the mechanism of detection for the test strip detection of nucleic acids by using the one-probe method.

FIG. 4 illustrates the fundamental principle for the test strip detection of nucleic acids by using a one-probe method.

Figure 5:
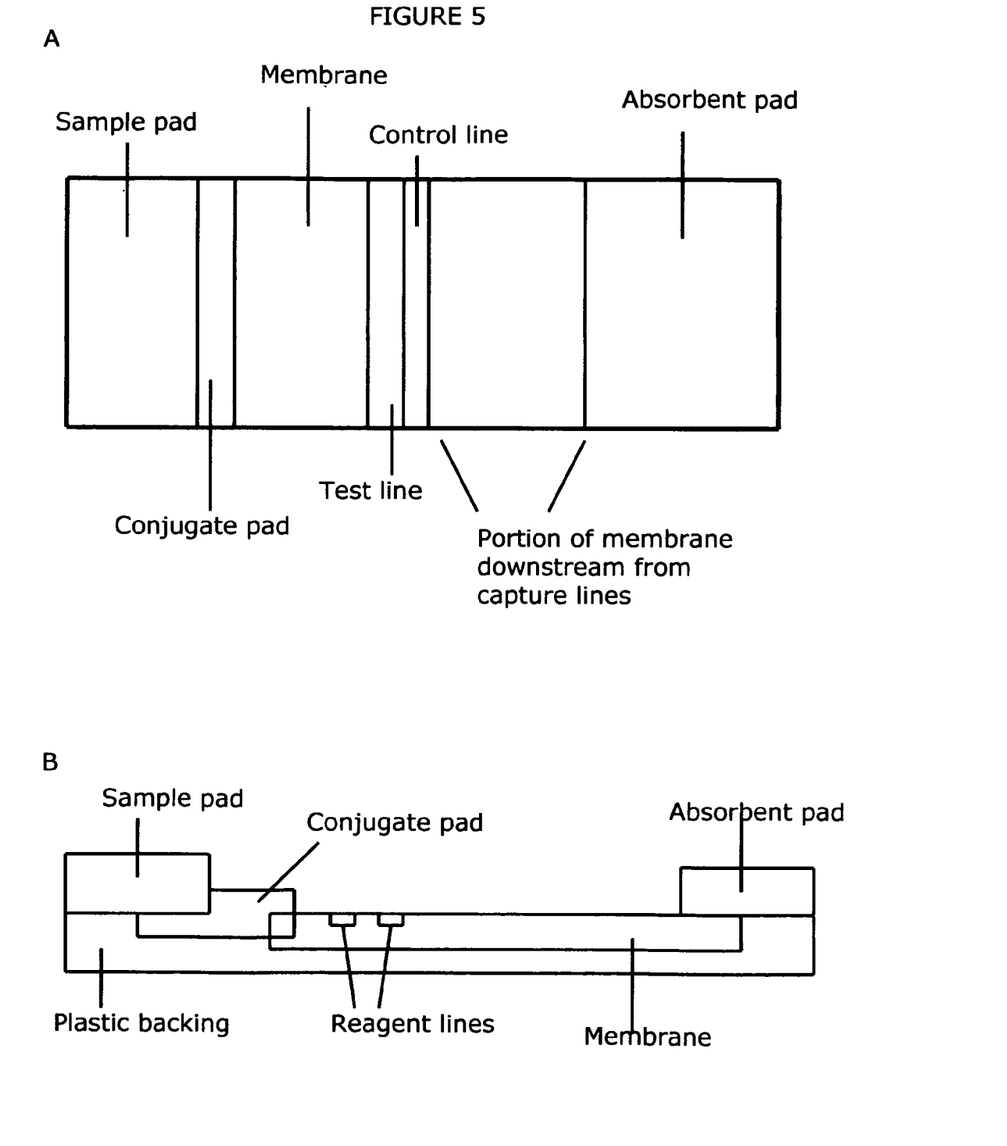
FIGS. 5A and 5B are illustrations of the basic structure of the test strip used or detecting nucleic acid amplification products.

FIG. 5 illustrates the basic structure of the test strip for detecting nucleic acid amplification products.

In a preferred embodiment of the present invention the test strip for detecting nucleic acid amplification products, comprises a sample pad (31), a chromatic particle conjugate pad (32), a fibrous membrane (23), and a water-absorbing filter paper pad (24) sequentially arranged on a liner (27) with non-drying adhesive, each part partially overlapping an adjacent one, and the fibrous membrane being also equipped with a detection line (25) and a quality control line (26). The chromatic particles on the chromatic particle conjugate pad (32) are coated with anti-A antibodies, the detection line (25) is coated with anti-B antibodies, and the quality control line (26) is provided with anti-A antibodies. The chromatic particles may be colloidal gold particles or latex particles, and the fibrous membrane can be a cellulose nitrate membrane or a nylon membrane.

Detailed descriptions of the test strip technique for rapid detection of nucleic acids and the structure of the test strip for detecting nucleic acids can be referenced in Chinese (App No. 200610003429.1)

As a universal technical platform for enclosed detection of nucleic acid amplification products, the method and device of the present invention can be widely applied to various fields such as detection of infectious pathogens, public health emergencies, livestock husbandry and food industry, customs inspection and quarantine, environment detection, biological weapon detection, human genetic disease detection, prenuptial and prenatal examination as well as prenatal and postnatal care, medicolegal and consanguinity expertise, and the like.

The enclosed nucleic acid amplification product detection device and method of the present invention can be used for the detection of common pathogens include bacteria, fungi, viruses, mycoplasmas, chlamydiae, parasites, and so on. The enclosed nucleic acid amplification product detection device can discriminate not only the pathogens, but also subtypes including virulent strains, mutant strains, and drug resistant strains.

The enclosed nucleic acid amplification product detection device and method of the present invention can be used for public health emergencies. Many countries have invested heavily to establish a nation-wide infectious disease prevention and control system, wherein quick diagnostic reagents for detecting fulminating infectious diseases will be used as conventional reserve in the centers of the system, so that pathogens can be rapidly discriminated and effectively controlled upon public health emergencies. Detection objects of this aspect include, for example, bird flu, SARS, cholera, plague, anthrax, Ebola, epidemic hemorrhagic fever (EHF), and the like. The enclosed nucleic acid amplification product detection device and method of the present invention can be used in food industry, agriculture as well as livestock husbandry. Due to frequent alimentary toxicoses, it is often necessary to perform detection on milk, beverages, and meat products before they leave factory with respect to certain bacteria such as fungi, colibacilluses, salmonellae, botulinuses, and the like. Also, differential diagnosis of microbes harmful to main farm crops will bring overwhelming economic and social benefits. The device and methods of the present invention finds a promising market in disease diagnosis for livestock, fish, and domestic fowls.

In another aspect, the enclosed nucleic acid amplification product detection device of the invention can be used in customs import-export quarantine control, which is also a stable and reliable market. For example, in the case of import in foreign trade, there is a demand on a complete set of quick diagnostic systems being sensitive and reliable, in order to prevent alien harmful microbes, pest eggs, and transgene products from flowing from one country to another. In the case of foreign trade export, by providing an importing country with a set of completed quarantine profiles, foreign trade export of agricultural, forestry, and food products will be greatly promoted, and trade disputes will be decreased.

The enclosed nucleic acid amplification product detection device and method of the present invention can be used can be used in detection and discrimination of microbes harmful to soil, water sources, air, and other environments. A set of on-site inspection methods that are easy, sensitive, and rapid will be greatly significant to environment detection.

The enclosed nucleic acid amplification product detection device and method of the present invention can be used can be used for detecting biological weapons. Techniques for biological weapon detection are being developed by countries all over the world. Common biological weapon pathogens include cholera, plague, anthrax, Ebola, epidemic hemorrhagic fever (EHF), artificially modified bacteria and viruses, and the like.

Another use for the enclosed nucleic acid amplification product detection device and method of the present invention is for detecting gene mutations. Many human diseases are the result of genetic mutations. Research on single nucleotide polymorphism (SNP), has revealed that each individual has a unique genome and thus each individual's susceptibility to diseases and sensitivity to drugs is unique. As a result, "personalized medicine" is finding great applicability in predicting susceptibility to major diseases, and determining precise administration of drugs for each individual according to his/ her sensitivity and efficacy to a given drug as determined by the unique genotype of his/her own. As there are hundreds of common diseases caused by gene mutations including gene deficiency, gene transposition, and the like, the enclosed nucleic acid amplification product detection unit of the invention can be used for diagnostics for human genetic diseases.

Finally the enclosed nucleic acid amplification product detection device and method of the present invention can be used in prenuptial examination, prenatal examination, prenatal postnatal care, DNA determination of blood, semen, hairs, and other samples from crime scenes, DNA determination of criminal suspects, consanguinity, gene ID card, populational gene database, and the like.

Compared with conventional PCR detection techniques, the devices and methods of the present invention disclosed provide for enclosed detection. The detection unit may be enclosed by both interior and exterior walls, that achieve a double sealing effect is achieved Sealing the device's inner core prevents the need to uncover the reaction tube which prevents the amplification product from leaking out, thereby minimizing the chance of contamination from the amplification product and the occurrence of false positives in subsequent detection is prevented. The sealing ring for the fixing case ensures that the amplification product will not flow back into the fixing case, thereby the fixing case is essentially free from contamination. Moreover, a triplex sealing diaphragm on the base ensures that the amplification product will not flow back into the bottom of the washing buffer vacuole tube through the glass fiber paper; Sealing the device's outer enclosure, composed of the outer casing, the handle cover, and the transparent window, constitutes a totally enclosed environment, and cannot be reopened once it is fastened during experiment, thereby preventing the amplification product inside the device from leaking out.

The methods of the present invention provide high specificity. By adding two specific primers together with 1 or 2 specific probes into the amplification reaction, the detection reaction may be highly specific.

The methods of the present invention provide high sensitivity of target nucleic acid amplification product detection after amplification. The methods of the present invention are simple and provide rapid operability. The whole detection process takes as little as 10 to 15 minutes, compared to at least 1 hour required by conventional agarose gel electrophoresis The technical scheme of the invention will now be further described by the following embodiments. The embodiments are illustrative only and shall not be construed as limiting the protection extent of the invention.

EXAMPLES

Example 1

Detecting a Product of PCR Amplification of Target Nucleic Acids in Gonococci

1. PCR Amplification:

| | |
|---|---|
| KCl (500 mmol) | 2 µL |
| Tris-HCl (pH 8.3, 100 mmol) | 2 µL |
| MgCl$_2$ (20 mmol) | 2 µL |
| dNTP (2 mmol) | 2 µL |

-continued

| | |
|---|---|
| Forward Primer (Biotin-labeled, 2 µmol) 5'Biotin-CAT ACT GTA CCA TAG CGT T | 2 µL |
| Reverse Primer (2 µmol) 5'ATT CTG ACA TCC CAA GCT T | 2 Ml |
| Reverse FITC-labeled probe (2 µmol) | 2 µL |
| Gonococci | 4000 |
| Taq DNA Polymerase | 0.5 units |
| Total | 20 µL |
| 95 DEG C. | 5 s |
| 60 DEG C. | 15 s |
| 72 DEG C. | 15 s |
| 60 cycles | |

2. Detection placing the PCR tube containing the amplification product inside the hole for housing the PCR tube in the fixing case (wherein washing buffer vacuoles have already been provided in the hole for housing the washing buffer vacuole tube in advance);

fastening the fixing case, and placing it inside the detection unit;

closing the handle cover of the detection unit;

pressing the cover of the detection unit until it is fastened down;

determining the result after 10 minutes;

recording the detection result, and discarding the enclosed detection unit in a safety place as a whole.

Figure 6:
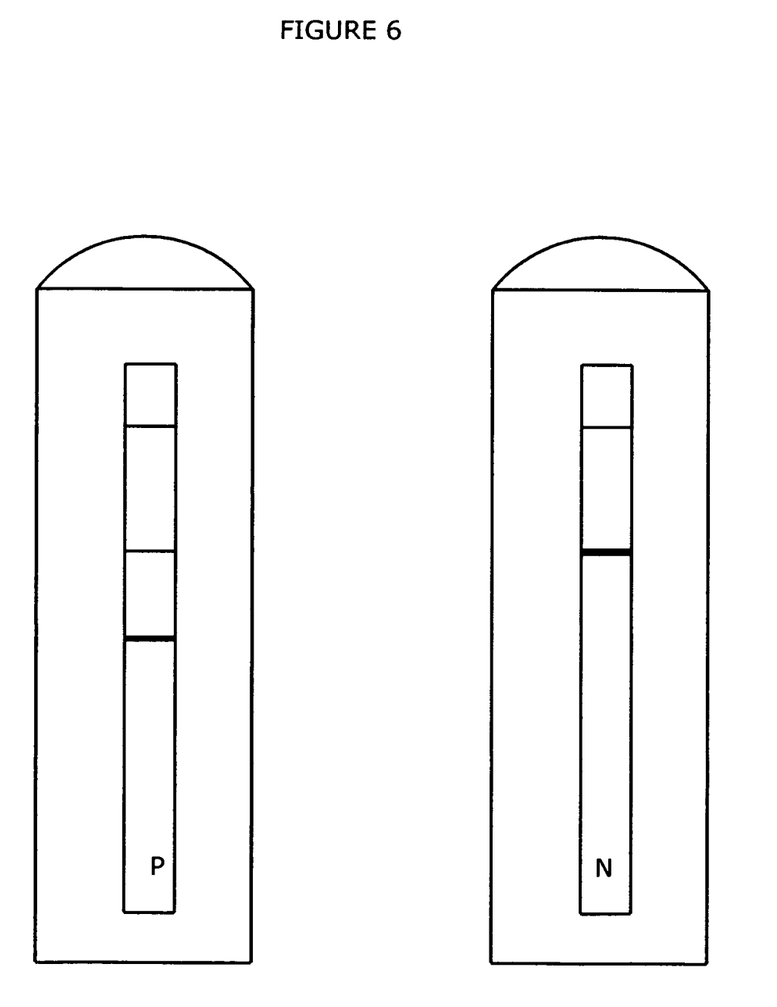
FIG. 6 is a representation that demonstrates the detection of gonococci utilizing the device and PCR amplification

The detection result of Example 1 is as shown in FIG. 6, wherein the detection line (line T) turns red in the case of a positive sample, while remaining colorless in the case of a negative sample, and the quality control line (line C) turns colored in both cases to indicate that the result is valid.

Example 2

Detecting a Product of Isothermal Amplification (A Method for Amplifying a Target Nucleic Acid Sequence by Using Nickase and a Kit for Amplifying a Target Nucleic Acid Sequence, of Target Nucleic Acids Using Cloned DNA in Gonococci as the Template 1. Reaction Conditions:
Tube 1:

| | |
|---|---|
| Reactive buffer solution 10 × (1000 mM NaCl, 500 mM Tris-HCl, 100 mM MgCl$_2$, 10 mM dithiothreitol, PH 7.9 at 25 DEG C.) | 1 µL |
| Two pairs of primers P1,2/S1,2 5 µmol/0.5 µmol | 2 µL |
| 5'TCC AGA CTT <u>GAG TCG</u> GAT GCT TCT TAG GGA CGC A | |
| 5'AAT GCA TGT <u>GAG TCG</u> GAT GGA TAT GTC CAA TCC TA | |
| Ultrapure water | 5 µL |

-continued

| | |
|---|---|
| Template gonococcal plasmids (1000 copies/muL) | 2 μL |
| Total | 10 μL |

Denatured at 95 DEG C for 10 minutes, then naturally cooled to room temperature.
Tube 2:

| | |
|---|---|
| Reactive buffer solution 10x(1000 mM NaCl, 500 mM Tris-HCl, 100 mM MgCl$_2$, 10 mM dithiothreitol, PH 7.9 at 25 DEG C.) | 1 μL |
| dNTP 2 mmol/ | 2 μL |
| Labeled probe | 2 μL |
| Bovine serum albumin 100 ng/μL | 2 μL |
| Nickase N.BstNB I 10 units/μL | 0.5 μL |
| Bst DNA polymerase 8 units/μL | 0.25 μL |
| Ultrapure water | 2.25 μL |
| Total | 10 μL |

The reaction mixtures in tube 1 and tube 2 are mixed uniformly, held in a metal bath at 54 DEG C for 30 minutes, denatured at 95 DEG C for 5 minutes, naturally cooled to room temperature, and then subjected to detection.

2. Detection placing the PCR tube containing the amplification product inside the hole for housing the PCR tube in the fixing case (wherein washing buffer vacuoles have already been provided in the hole for housing the washing buffer vacuole tube in advance);

fastening the fixing case, and placing it inside the detection unit;

closing the handle cover of the detection unit;

pressing the cover of the detection unit until it is fastened down;

determining the result after 10 minutes;

recording the detection result, and discarding the enclosed detection unit in a safety place as a whole.

Figure 7:
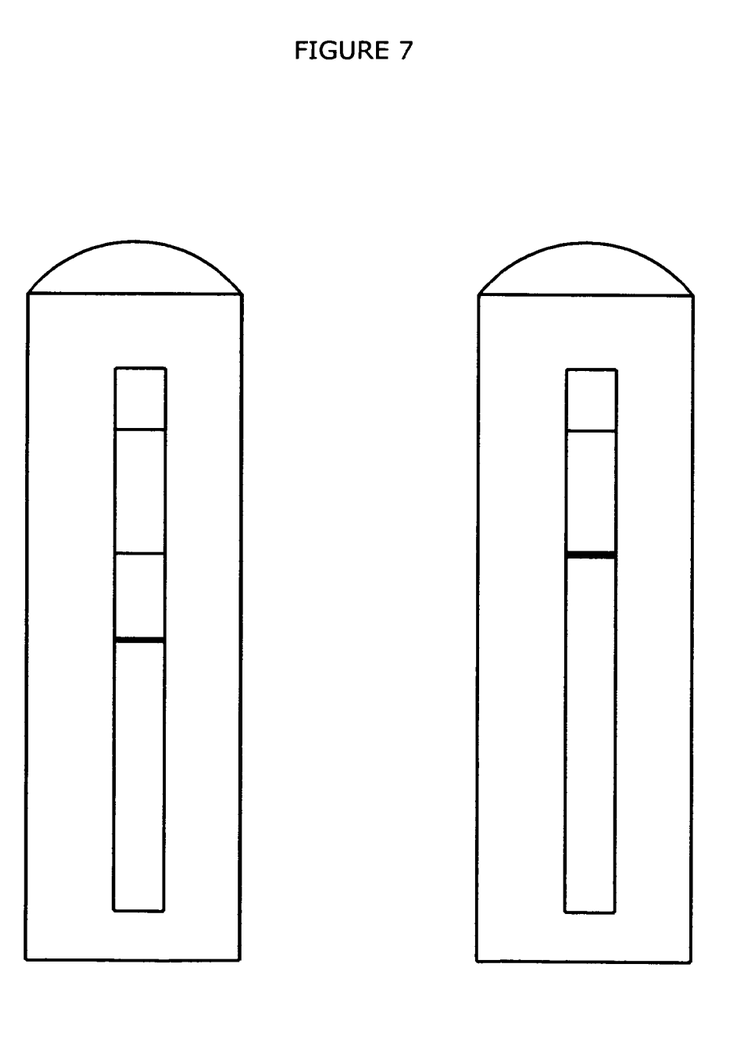
FIG. 7 is a representation that demonstrates the detection of gonococci utilizing the device and isothermal amplification

The detection result of Example 2 are as shown in FIG. 7, wherein the detection line (line T) goes red in the case of a positive sample, while remaining colorless in the case of a negative sample, and the quality control line (line C) turns colored in both cases to indicate that the result is valid.

Example 3

Detection and Typing of Mononucleotide Polymorphism of Mitochondrial DNA G11778A Associated with Leber's Disease Leber's hereditary optic neuropathy (LHON) is a maternally inherited binocular optic nerve disease. It was firstly reported by Wallace in 1988 that a primary point mutation (G to A) at the mitochondrial DNA (mtDNA) nucleotide site 11778 can cause LHON. So far, there has been 25 mtDAN site mutations found to be associated with this disease. Reports in recent years have shown that LHON patients with primary site mutations at 3460, 14484, etc. and LHON patients with coexisted primary and subsequent site mutations all have clinical manifestations similar to those with site mutation at 11778, and consequently, it is difficult for doctors to discriminating the patients according to their clinical manifestations. As a result, molecular biological gene detection has become the most preferred method for determining a Leber's disease caused by different factors. Regarding the diagnostic significance for LHON provided by the typing of mitochondrial site G11778A, an enclosed nucleic acid amplification product detection unit for detecting SNP for detecting polymorphism of site G11778A.

1. Sampling

5 μl of peripheral venous anticoagulation blood was removed from a subject (frozen), using a kit for quick extraction of DNA in minute quantities produced by Ustar Biotechnologies (Hangzhou) Ltd. to carry out nucleic acid extraction for subsequent gene amplification.

2. PCR

In order to eliminate interference on mitochondrial gene amplification by pseudo genes in gene groups, the amplification was performed twice, wherein the product of the first amplification is used as the template for the second amplification, and the product of the second amplification is subsequently used for SBE SPELL THIS OUT <Single Base Extention>.

| | |
|---|---|
| Primers: | 0.2 μmol |
| Primers for the first amplification: | |
| Nd4P_out_F | 5' TCACTCTCACTGCCCAAAA 3' |
| Nd4P_out_R | 5' GGAGAATGGGGGATAGGTGT 3' |
| Primers for the second amplification: | |
| Nd4P_in_F | 5' CTTCACCGGCGCAGTCATTC 3' |
| Nd4P_in_R | 5' AGGCGAGGTTAGCGAGGCTT 3' |
| dNTP: | 0.2 mmol |
| Buffer solution: | |
| MgCl2 | 3 μmol |
| KCl | 50 μmol |
| Tris-HCl (PH 9.0) | 10 μmol |
| Triton-100 | 1.0% |
| Taq DNA polymerase | 0.8 units |
| Total | 20 μL |
| PCR reaction procedure: | |
| PCR with the first pair of primers: | 95 DEG C. 5 mm |
| 35 cycles of: | 94 DEG C. 30 s, |
| | 55 DEG C. 45 s, |
| | 72 DEG C. 60 s |

-continued

|  | 72 DEG C. | 5 min |
|---|---|---|
| PCR with the second pair of primers: | 95 DEG C. | 5 min |
| 35 cycles of: | 94 DEG C. | 30 s, |
|  | 65 DEG C. | 30 s, |
|  | 72 DEG C. | 30 s |
|  | 72 DEG C. | 5 min |
| Size of the products: | 801 bp (with the first pair of primers) | |
|  | 182 bp (with the second pair of primers) | |

3. Degrading the Remaining dNTP in the Second PCR Amplification

| Template: the above PCR amplification product | 20 μL |
|---|---|
| Buffer solution: | |
| Bis Tris-Propane | 50 mmol |
| MgCl$_2$ | 1 mmol |
| ZnCl$_2$ | 0.1 mmol |
| Thermosensitive phosphatase | 1 unit |
| Total | 30 μL |

Reaction procedure: 37 DEG C., 15 min
Thermosensitive phosphatase inactivation: 80 DEG C., 20 min 4. Single Base Extension (SBE) (Detecting G and A):

Template: the PCR amplification product after the above dNTP degradation 30 μL

| Extension primer: |  | 0.1 μmol |
|---|---|---|
| 5' FITC-TCAAACTACGAACGCACTCACAGTC 3' (Forward) Biotin-ddGTP/Biotin-ddATP |  | 0.5 μmol |
| Buffer solution: |  |  |
| Tris-HCL(pH 9.5) |  | 26 mmol |
| MgCl2 |  | 6.5 mmol |
| Thermal sequencing enzyme: |  | 0.5 units |
| Total |  | 40 μL |
| SBE reaction procedure: | 95 DEG C. | 60 s |
|  | 72 DEG C. | 90 s |

5. Detection
   placing the PCR tube containing the SBE reaction product inside the hole for housing the PCR tube in the fixing case (wherein washing buffer vacuoles have already been provided in the hole for housing the washing buffer vacuole tube in advance);
   fastening the fixing case, and placing it inside the detection unit;
   closing the handle cover of the detection unit;
   pressing the cover of the detection unit until it is fastened down;
   determining the result after 10 minutes;
   recording the detection result, and discarding the enclosed detection unit in a safety place as a whole.

Figure 8:
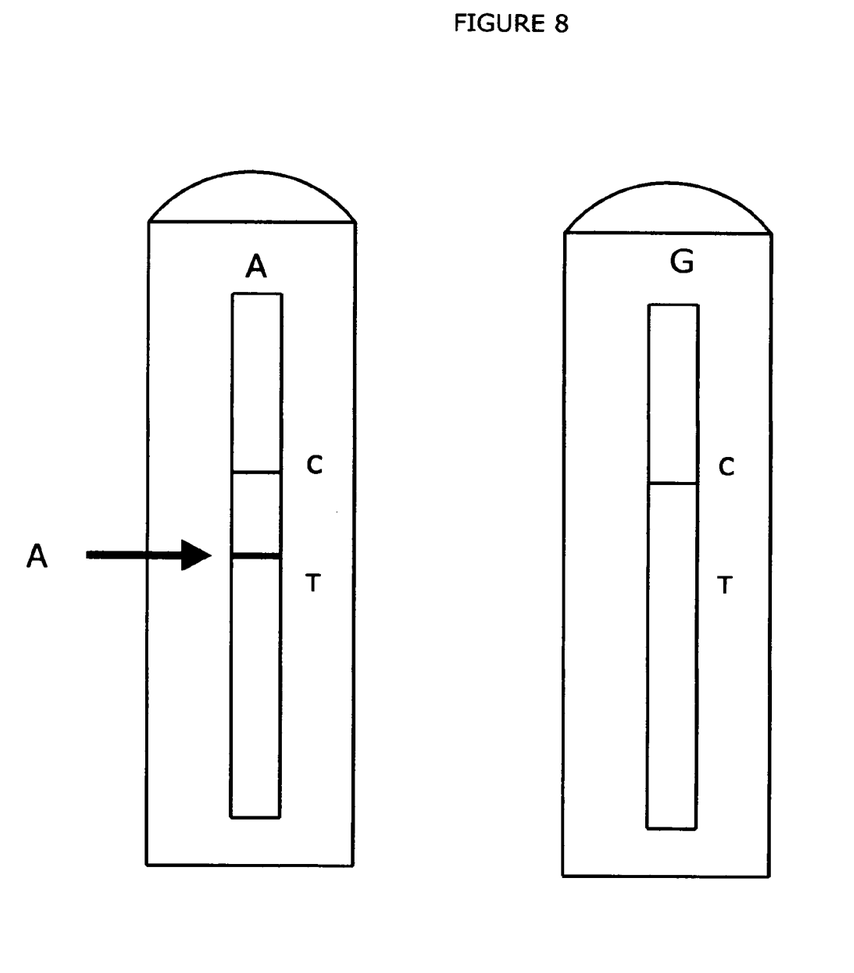
FIG. 8 is a representation that demonstrates the result of the mononucleotide polymorphism detection by using the enclosed nucleic acid amplification product detection device which indicates a G to A mutation at site 11778 in mitochondrial ND4 gene.

The result of the mononucleotide polymorphism detection by using the enclosed nucleic acid amplification product detection device is as shown in FIG. 8, which indicates a G to A mutation at site 11778 in mitochondrial ND4 gene. The result is in consistence with the sequencing result.

We claim:

1. A device for detection of a target nucleic acid amplification product comprising a cassette having a first port into which a container containing the target nucleic acid amplification product in a fluid is placed such that a portion of the container is exposed, a second port into which a washing buffer container containing washing buffer is placed, a sealable outer casing into which the cassette is placed and which completely encompasses the cassette when the outer casing is sealed, a cutting device that punctures the exposed portion of the container containing the target nucleic acid amplification product and a puncture needle which punctures the washing buffer container when the sealable outer casing is sealed to release the fluid and the washing buffer onto glassfiber paper such that the fluid and washing buffer are mixed and a detection strip contiguous with the glassfiber paper such that the washing buffer and liquid contacts the detection strip after the container and washing buffer container are punctured.

2. The device of claim 1, wherein the target nucleic acid amplification product remains within the device once the container is punctured and wherein the device cannot be re-opened.

3. An enclosed device for detection of a target nucleic acid amplification product, comprising an inner core (1) and an outer casing (15), wherein the inner core (1) comprises a fixing case (2) and a base (5), the fixing case (2) having two ports respectively for housing washing buffer vacuoles (3) and a reaction tube (11) containing an amplification product in a fluid (7), the base (5) comprising a washing buffer container (21) having a vacuole puncture needle (4), an amplification product container (22) having a blade (9), a sealing diaphragm (6), a piece of glassfiber paper (8), and a test strip sealing part (14) having a test strip (13) sealed therein and a transparent window (12) and wherein the outer casing (15) comprises a handle cover (16), a fixing case pressing part (17), a washing buffer vacuole extruding part (18), and a transparent window (20) wherein the blade punctures the exposed portion of the container containing the target nucleic acid amplification product and the vacuole puncture needle punctures the washing buffer container when the sealable outer casing is sealed thereby releasing the fluid and the washing buffer onto the glassfiber paper such that the fluid and washing buffer are mixed and thereby flow the detection strip.

4. An enclosed unit for rapid detection of a target nucleic acid amplification product, comprising an inner core (1) and an outer casing (15), wherein the inner core (1) comprises a fixing case (2) and a base (5), the fixing case (2) having two ports respectively for housing washing buffer vacuoles (3) and a reaction tube (11) containing an amplification product (7), the base part (5) comprising a washing buffer container (21) having a vacuole puncture needle (4) for puncturing the washing buffer vacuoles (3), an amplification product container (22) having a blade (9) for cutting the container (22), a sealing diaphragm (6) between the units (21) and (22), a piece of glassfiber paper (8) disposed in the container elements (21) and (22) and connected to the bottom of a test strip (13), and a test strip sealing part having the test strip (13) sealed therein and a transparent window (12) for observing the test strip (13) and the outer casing (15) comprises a handle cover (16), a fixing case pressing part (17), a washing buffer vacuole extruding part (18), and a transparent window (20) wherein the blade punctures the exposed portion of the container containing the target nucleic acid amplification product and the vacuole puncture needle punctures the washing buffer container when the sealable outer casing is sealed thereby releasing the fluid and the washing buffer onto the glassfiber paper such that the fluid and washing buffer are mixed and thereby flow the detection strip.

5. The device of claim 1, further comprising a sealing ring (10) positioned between the port for housing the reaction tube (11) and the base (5), such that the amplification product will not flow back into the fixing case (2).

6. The device of claim 3, further comprising a sealing ring (10) positioned between the port for housing the reaction tube (11) and the base (5), such that the amplification product will not flow back into the fixing case (2).

7. The device of claim 4, further comprising a sealing ring (10) positioned between the port for housing the reaction tube (11) and the base (5), such that the amplification product will not flow back into the fixing case (2).

8. The device of claim 6, further comprising a sealing diaphragm (6) comprising three alternating layers vertically disposed such that the amplification product will not flow back into the fixing case (2), while being mixed with the washing buffer flowing in a single direction and adsorbed by the test strip (13).

9. The device of claim 7, further comprising a sealing diaphragm (6) comprising three alternating layers vertically disposed such that the amplification product will not flow back into the fixing case (2), while being mixed with the washing buffer flowing in a single direction and adsorbed by the test strip (13).

10. The device of claim 6, wherein the outer casing (15) cannot be reopened once it is closed so as to prevent the target nucleic acid amplification product from leaking out of the device.

11. The device of claim 7, wherein the outer casing (15) cannot be reopened once it is closed so as to prevent the target nucleic acid amplification product from leaking out of the device.

* * * * *